United States Patent [19]
Muller et al.

[11] Patent Number: 5,807,305
[45] Date of Patent: Sep. 15, 1998

[54] IONTOPHORESIS DEVICE COMPRISING AT LEAST ONE ELECTRODE ASSEMBLY WITH A REVERSIBLE COMPOSITE ELECTRODE

[75] Inventors: Daniel Muller, Pau; Henry Saunal, Montpellier, both of France

[73] Assignees: Sanofi; Elf Aquitaine, both of France

[21] Appl. No.: 776,184
[22] PCT Filed: Jul. 25, 1995
[86] PCT No.: PCT/FR95/00995
  § 371 Date: Mar. 11, 1997
  § 102(e) Date: Mar. 11, 1997
[87] PCT Pub. No.: WO96/03179
  PCT Pub. Date: Feb. 8, 1996

[30] Foreign Application Priority Data

Jul. 26, 1994 [FR] France .................................. 94 09231

[51] Int. Cl.$^6$ ........................................................ A61N 1/30
[52] U.S. Cl. .............................................. 604/20; 607/115
[58] Field of Search ........................... 607/115, 149–153; 604/20–21

[56] References Cited

U.S. PATENT DOCUMENTS 5,320,731  6/1994  Muller et al. ........................... 204/299
5,543,098  8/1996  Myers et al. .

*Primary Examiner*—Mark Bockelman
*Attorney, Agent, or Firm*—Bacon & Thomas

[57] ABSTRACT

An iontophoresis device in which at least one of the electrodes is a composite electrode containing a polymeric binder, a powdered or fibrous conductive filler and a divided material capable of being consumed by electrochemical oxidation or reduction. The binder of the composite electrode consists of a polymer containing 10–100 mo % of 1,2-epoxypropane and/or 1,2-epoxybutane, and 40–0 mol % of at least one other monomer that is copolymerizable with such oxides. The device is useful for transcutaneously delivering active principles to a patient.

38 Claims, No Drawings

IONTOPHORESIS DEVICE COMPRISING AT LEAST ONE ELECTRODE ASSEMBLY WITH A REVERSIBLE COMPOSITE ELECTRODE

BACKGROUND OF THE INVENTION

1. Field of the Invention

The invention relates to an iontophoresis device for the transcutaneous administration of an active principle to a subject, which device comprises at least one electrode assembly provided with a reversible composite electrode. It also relates to the said electrode assembly.

2. Description of Related Art

In the current treatment of numerous conditions, it is necessary to administer a medicament or other active principle to a subject in a controlled and often prolonged manner. Among the numerous techniques available to the formulation pharmacist, that of iontophoresis represents an advantageous alternative for controlling the administration of active principles, such as medicinal substances, into the body of the subject. One such technique comprises the use of an electric current for controlling the amount but also the rate of delivery of an active principle through the skin of a subject. In numerous cases, this technique proves to be highly effective in significantly increasing the supply of active principle due to the current, in comparison with the amount delivered without a current.

The transcutaneous administration of an active principle by iontophoresis to a subject is generally performed, starting with an aqueous solution or an aqueous gel containing the active principle in an at least partially ionized form or in a neutral form, by applying an electric signal between, on the one hand, a first electrode, called the active electrode, which has the same polarity as the ions of the active principle to be administered or a positive polarity if the active principle is neutral and which is found in contact with a reservoir element, which contains the active principle and is placed in contact with a first area of the skin of the subject, and, on the other hand, a second electrode, called the back electrode or passive electrode, of opposite polarity to that associated with the active principle, which is placed, directly or via an indifferent electrolyte, in contact with a second area of the skin of the subject which is separate from the first area. During the passage of the current, generated by application of a voltage between the electrodes, in the circuit thus produced, the ions of the active principle migrate away from the electrode of the same polarity (active electrode) through the skin and the tissues of the subject towards the electrode of opposite polarity (back electrode) and are thus found to pass into the circulatory system of the subject. Likewise, the neutral molecules of active principle are carried away from the positive electrode in the aqueous electroosmotic flux through the skin and the tissues of the subject towards the negative electrode (back electrode) and are thus also found to pass into the circulatory system of the subject.

One iontophoresis device for the transcutaneous administration of an active principle to a subject is of the type comprising a first electrode assembly composed of a first electrode, called the active electrode, in contact with an active reservoir element adapted, on the one hand, in order to contain an electrolyte holding the active principle in an at least partially ionized form or in a neutral form, and, on the other hand, in order to ensure, when it is placed in contact with an area of the skin of the subject, ionic conducting continuity between the said first electrode and the said area, a second electrode assembly composed either (i) of a second electrode, called the back electrode, or alternatively, and preferably, (ii) of such a second electrode in contact with a reservoir element arranged in order to hold an electrolyte and in order to ensure, when it is placed in contact with a portion of the skin of the subject, ionic conducting continuity between the second electrode and the said portion, and an electric signal generator which can be connected to each of the said first and second electrodes so that the first electrode has the same polarity as the ions of the active principle or a positive polarity if the said active principle is neutral and so that the second electrode has a polarity opposite to that of the first electrode.

The iontophoresis electrodes intended to apply electric signals to medicinal reservoirs, in order to promote transdermal passage of the active principles, must meet the following conditions:

good electronic conductivity, in order for the potential applied at the connection between the electric signal generator to be distributed uniformly over the whole surface of the reservoir and thus over the whole surface in contact with the skin;

electrochemical reversibility, that is to say absence of activity overpotential and absence of side reactions with the electrolyte, in particular avoiding the electrolysis of the water always present by the very nature of the medicinal reservoir and/or via perspiration, and, in addition, absence of corrosion.

For many years, electrochemists have used, as biological probes or as reversible iontophoresis electrodes, silver/silver chloride (Ag/AgCl) electrodes which are obtained in particular by direct chloridation of a silver film, wire or grid according to conventional electrochemical processes for anodic oxidation in aqueous solutions which are rich in chlorides, for example HCl, NaCl or others. These electrodes, obtained by chloridation, are satisfactory from an electrochemical viewpoint but they exhibit, however, the following disadvantages:

the electrochemical chloridation is fairly slow and problematic if it is desired to obtain good quality deposition of chloride, it is poorly suited to continuous processes and to the production of non-chloridated areas of possibly complex shapes which it is desirable to insert in order to make possible permanent contact sockets with the signal generator;

a large excess of silver metal is necessary in order to make possible both chloridation to the desired level, generally from approximately 0.5 mg/cm$^2$ to 16 mg/cm$^2$, i.e. that which causes the passage of an amount of electricity from 0.1 to 3 mAh (0.36 to 10.8 coulombs) per cm$^2$ of electrode, and also satisfactory mechanical strength of the electrode;

as soon as the amount of silver chloride exceeds approximately 10 mg per cm$^2$, which corresponds to approximately 2 milliampere-hour per cm$^2$, the adhesion of the silver chloride to its support is very poor and this silver chloride risks becoming detached from the support at the least mechanical stress, rendering the electrode irreversible;

the electrochemical use of silver chloride initially formed is only partial because its reduction, when the electrode is used as a negative electrode, preferentially takes place at the Ag/AgCl interface, which further weakens the cohesion of the assembly and renders this electrode irreversible long before the silver chloride has become exhausted.

Owing to the fact that the electrodes are disposable in each iontophoretic treatment, the notion of cost becomes paramount. The electrodes based on films of chloridized silver are expensive because the material cost, which is due to an excess of metallic silver and of silver chloride which are essential for good reproducibility, and because of their non-continuous and necessarily slow method of manufacture, because the chloridation of the silver must be carried out at a low current density, generally of less than 5 mA per $cm^2$, in order to obtain good quality deposition of AgCl.

Electrode assemblies for iontophoresis are known comprising a composite electrode, for example based on silver and/or on silver chloride, in contact with a reservoir element adapted, on the one hand, in order to contain an electrolyte, which holds an active principle in an at least partially ionized form or in a neutral form, if the associated electrode is the active electrode, or alternatively which contains an indifferent electrolyte, if the associated electrode only acts as the back electrode, and, on the other hand, in order to ensure, when it is placed in contact with an area of the skin of the subject, ionic conducting continuity between the said composite electrode and the said area. The composite electrode is formed from a composition composed of a polymer binder and, by volume of the said binder, from 5% to 40% of a conductive filler, in particular carbon black or graphite fibres, forming a conductive network within the polymer binder, and from 5% to 40% of a divided material consumable by electrochemical oxidation or reduction. Such electrode assemblies and the iontophoresis devices which include them are described in particular in the citation WO-A-9116944. When the electrode of the electrode assembly is intended to act as anode, the electrochemically consumable material is consumed by oxidation and comprises an electrochemically oxidizable metal, such as Ag, Zn, Cu, Ni, Sn, Pb, Fe or Cr, the metals Ag, Zn and Cu being very particularly preferred. When the electrode of the electrode assembly is intended to act as cathode, the electrochemically consumable material is consumed by reduction and generally comprises an ionizable metal compound, the metal ions of which are electrochemically reducible. Mention may advantageously be made, among these metal compounds, of silver halides and hexacyanoferrate and copper halides and very particularly AgCl and CuCl. The polymers capable of constituting the polymer binder of the composite electrode can be such as polyalkenes, polyisoprene, poly(vinyl acetate), ethylene/vinyl acetate copolymers, polyamides, polyurethanes, poly(vinyl chloride), cellulose polymers, polyoxyethylene or polymers of acrylic acid. Ethylene/vinyl acetate (abbreviated as "EVA") copolymers are the preferred copolymers.

With respect to the iontophoresis electrodes composed of a film of an electrochemically consumable material, for example, metal such as copper, zinc or silver and/or metal salt such as CuCl or AgCl, deposited on a support, the corresponding composite electrodes as described in the citation WO-A-9116944 have markedly improved mechanical properties. These composite electrodes exhibit good flexibility and neither detachment nor tearing of the composite electrode layer during use is observed. In addition, the amount of electrochemically consumable material to be used in order to produce the composite electrode is smaller than that to be used in order to form the corresponding non-composite iontophoresis electrode, because it is no longer necessary to have an excess of the electrochemically consumable material, in particular an excess of metal, in order to ensure the mechanical strength of the electrode, the said mechanical strength being contributed by the polymer binder; the result is therefore a decrease in the material cost.

Despite their advantages with respect to the conventional reversible electrodes used in iontophoresis, the composite electrodes provided for in the citation WO-A-9116944 still exhibit a number of inadequacies. In particular, it is difficult to prepare such composite electrodes having a thickness of less than 100 $\mu$m, that is to say a capacity of less than 2 ma-hour. Moreover, these composite electrodes are virtually not invertible. "Invertible electrodes" is understood to mean, according to the invention, electrodes which can be used over a number of oxidation and reduction cycles resulting from one or a number of changes in polarity during the iontophoretic treatment. In addition, it is very difficult or even, in the case of an EVA polymer binder, virtually impossible to obtain the said composite electrodes by a spreading technique via the solvent route.

SUMMARY OF THE INVENTION

It has now been found that it is possible to overcome the disadvantages of the composite electrodes for iontophoresis of the type of those described in the citation WO-A-9116944 by constituting the polymer binder of the said electrodes from a specific polymer containing, in polymerized form, from 60% to 100%, on a molar basis, of 1,2-epoxypropane and/or 1,2-epoxybutane and from 40% to 0%, on a molar basis, of one or a number of other monomers copolymerizable with 1,2-epoxypropane and/or 1,2-epoxybutane.

The said composite electrodes, the polymer binder of which is composed of the abovementioned specific polymer based on 1,2-epoxypropane and/or 1,2-epoxybutane, in addition to the advantages of the composite electrodes of the citation WO-A-9116944, exhibit, inter alia, excellent invertibility and, moreover, they are highly suitable for production involving spreading techniques by the solvent route making it possible to obtain electrodes with thicknesses of less than 100 $\mu$m, that is to say having capacities of less than 2 ma-hour.

The subject of the invention is therefore an improved iontophoresis device comprising at least one electrode assembly equipped with a reversible composite electrode containing a polymer binder composed of a polymer as mentioned above based on 1,2-epoxypropane and/or 1,2-epoxybutane and the invention also relates to the said electrode assembly.

DETAILED DESCRIPTION OF THE INVENTION

The iontophoresis device according to the invention, for the transcutaneous administration of an active principle to a subject, is of the type comprising a first electrode assembly composed of a first electrode, called the active electrode, in contact with an active reservoir element adapted, on the one hand, in order to contain an electrolyte holding the active principle in an at least partially ionized form or in a neutral form, and, on the other hand, in order to ensure, when it is placed in contact with an area of the skin of the subject, ionic conducting continuity between the said first electrode and the said area, a second electrode assembly composed either (i) of a second electrode, called the back electrode, or alternatively, and preferably, (ii) of such a second electrode in contact with a reservoir element arranged in order to hold, at least, an electrolyte and in order to ensure, when it is placed in contact with a portion of the skin of the subject, ionic conducting continuity between the second electrode and the said portion, and an electric signal generator which can be connected to each of the said first and second electrodes, so that the first electrode has the same polarity as the ions of the active principle or a positive polarity if the said active principle is neutral and so that the second electrode has a polarity opposite to that of the first electrode, the first electrode in contact with the active reservoir element and/or the second electrode in contact with the reservoir element associated with it, being composed of a composite electrode formed from a composition comprising a polymer binder and, as percentages by volume of the said binder, from 4% to 60% of an electrochemically non-consumable pulverulent or fibrous conductive filler and from 4% to 100% of a divided material consumable by electrochemical oxidation or reduction and it is characterized in that the polymer binder of the composite electrode or of each of the composite electrodes comprises at least one polymer based on 1,2-epoxypropane and/or 1,2-epoxybutane and containing, in molar percentages, from 60% to 100% of 1,2-epoxypropane and/or 1,2-epoxybutane and from 40% to 0% of one or a number of other monomers copolymerizable with 1,2-epoxypropane and/or 1,2-epoxybutane.

The invention also relates to an electrode assembly for iontophoresis comprising a composite electrode in contact with a reservoir element adapted, on the one hand, in order to contain an electrolyte, the said electrolyte holding an active principle in an at least partially ionized form or in a neutral form or being an indifferent electrolyte, and, on the other hand, in order to ensure, when it is placed in contact with an area of the skin of a subject, ionic conducting continuity between the said composite electrode and the said area, which composite electrode is formed from a composition composed of a polymer binder, and, by volume of the said binder, from 4% to 60% of an electrochemically non-consumable pulverulent or fibrous conductive filler and from 4% to 100% of a divided material consumable by electrochemical oxidation or reduction, the said assembly being characterized in that the polymer binder of the composite electrode comprises at least one polymer based on 1,2-epoxypropane and/or 1,2-epoxybutane and containing, in molar percentages, from 60% to 100% of 1,2-epoxypropane and/or 1,2-epoxybutane and from 40% to 0% of one or a number of other monomers copolymerizable with 1,2-epoxypropane and/or 1,2-epoxybutane.

The polymers based on 1,2-epoxypropane (also known as 1,2-propylene oxide) and/or 1,2-epoxybutane (also known as 1,2-butylene oxide), among which the polymer or polymers constituting the polymer binder of the composite electrode are chosen, more particularly have a molar content of 1,2-epoxypropane and/or 1,2-epoxybutane ranging from 75% to 100%. The said polymers based on 1,2-epoxypropane and/or 1,2-epoxybutane are more especially homopolymers of 1,2-epoxypropane or of 1,2-epoxybutane or alternatively statistical copolymers, sequential copolymers or sequential copolymers containing statistical junctions of 1,2-epoxypropane and of 1,2-epoxybutane with one another and/or with one or a number of cyclic monomers chosen from the group formed from (i) cyclic oxides, the ring of which contains more than three members, and (ii) cyclic oxides of formula

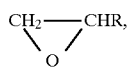

in which R is an $R_1$ radical or a $CH_2$—O—$R_2$—$R_1$ radical, with $R_1$ denoting a hydrogen atom or a $C_3$ to $C_{12}$, and preferably $C_3$ to $C_6$, alkyl or $C_2$ to $C_{12}$, and preferably $C_2$ to $C_6$, alkenyl radical and $R_2$ representing a polyether radical of formula —$(CH_2$—$CH_2$—O$)_p$— with p denoting a number ranging from 0 to 10 and preferably from 0 to 4.

Mention may be made, among the cyclic oxides (i) containing more than three members in the ring, of oxetane, tetrahydrofuran, dioxolane, dioxane and their substituted derivatives, in particular substituted by $C_1$ to $C_4$ alkyl radicals, such as methyl or ethyl. Mention may be made, among the cyclic oxides (ii) of formula

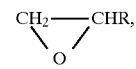

of those for which R represents a hydrogen atom or a propyl, butyl, —$CH_2OCH_3$ or —$CH_2OCH_2$—$CH$=$CH_2$ radical.

The polymers based on 1,2-epoxypropane and/or 1,2-epoxybutane constituting the binder of the composite electrode, where they are homopolymers or copolymers as defined above, can be crosslinked. The crosslinking can result, for example, from the action of a chemical generator of free radicals, in particular peroxide, azobisnitrile, sulphur or polysulphide, from the action of ionizing radiation, for example γ-radiation, or alternatively from the action of a triisocyanate or of a compound of a polyvalent element chosen from Al, Zn, Mg, Cd, Sn, B and Ti.

In the non-crosslinked state, the polymer or polymers based on 1,2-epoxypropane and/or 1,2-epoxybutane used to form the binder of the composite electrode have number-average molecular masses of between 10,000 and $10^6$ and more particularly ranging from 30,000 to 500,000.

The electrochemically non-consumable conductive filler which forms part of the composition of the composite electrode is composed in particular of a conductive material formed from at least one product such as carbon black, graphite or boron. The said filler and in particular the said material are provided in the form of a powder advantageously having a particle size of less than 100 μm and preferably of less than 50 μm or alternatively in the form of short fibres advantageously having a diameter ranging from 1 μm to 15 μm and a ratio of the length to the diameter, expressed in the same unit of length, ranging from 50 to 1000.

The electrochemically consumable material, which is associated with the polymer binder and with the electrochemically non-consumable conductive filler, must be a material consumable by electrochemical oxidation when the electrode is intended to act as anode or a material consumable by electrochemical reduction when the electrode is intended to act as cathode. The material consumable by electrochemical oxidation is advantageously a metal chosen from electrochemically oxidizable metals, such as Ag, Zn, Cu, Ni, Sn, Pb, Fe or Cr, the metals Ag, Zn and Cu being preferred. The material consumable by electrochemical reduction advantageously comprises an ionizable metal compound giving electrochemically reducible metal ions, the said metal compound being in particular a silver halide or hexacyanoferrate or a copper halide and very especially AgCl or CuCl. The electrochemically consumable material can also comprise the couple composed of an ionizable compound of a metal, giving metal ions electrochemically reducible to the metal, and of the said metal, as is the case, for example, with the AgCl/Ag couple.

When the composite electrode only contains a material consumable by electrochemical oxidation, it only becomes invertible after a first cycle of operating as an anode. If the consumable material of the composite electrode is only consumable by electrochemical reduction, the said electrode only becomes invertible after a first cycle of operating as a cathode. When the consumable material of the composite electrode is composed of a metal salt/metal couple, for example AgCl/Ag couple, the electrode can operate from the beginning without distinction as an anode or as a cathode.

The electrochemically consumable material contained in the composite electrode is provided in the form of a powder, the particle size of which is advantageously less than 100 $\mu$m and preferably less than 50 $\mu$m. In particular, the powder of the electrochemically consumable material exhibits a polymodal particle size distribution, that is to say is composed of a mixture of at least two powders of different particle sizes, each of the said particle sizes being in the particle size range of less than 100 $\mu$m and preferably of less than 50 $\mu$m.

It is possible to envisage depositing the electrochemically consumable material on the conductive filler in order to form a bifunctional material combining the function of the electrochemically consumable material and the function of the conductive filler and then incorporating the said bifunctional material in the polymer binder in order to form the composite electrode. Thus, it could be possible to produce carbon or graphite fibres coated with a metal which is consumed by electrochemical oxidation and to incorporate the fibres thus coated in the polymer binder in order to form the composite electrode.

The proportions of electrically non-consumable conductive filler and of electrochemically consumable material which are associated with the polymer binder in order to form the composite electrode represent, by volume of the polymer binder, 4% to 60% and more especially 8% to 45% for the conductive filler and 4% to 100% and preferably 25% to 70% for the electrochemically consumable material.

The composite electrodes used according to the invention can be prepared by resorting to any technique for obtaining thin films containing a polymer binder and in particular by using the technique of coating on a support film, a technique which can be compared with the application of a paint. Flat, flexible and thin composite electrodes are thus obtained which are well suited to use by application on the skin.

In the said coating technique, a fluid phase is first of all prepared which contains, in appropriate proportions, within the ranges defined above, the polymer based on 1,2-epoxypropane and/or 1,2-epoxybutane, which is intended to constitute the polymer matrix of the composite electrode, the electrochemically non-consumable conductive filler and the electrochemically consumable material and then a layer of the said fluid phase is deposited, by coating, on a support, the said layer, after cooling and/or evaporation of the volatile materials, constituting the composite electrode.

When the polymer based on 1,2-epoxypropane and/or 1,2-epoxybutane is sufficiently fluid, at working temperatures, to form a fluid mixture with the other constituents of the composite electrode, such a mixture can be used for the deposition of the layer on the support by coating.

The fluid phase from which the composite electrode layer is formed on the support by coating advantageously comprises a dispersion of the conductive filler and of the electrochemically consumable material in a solution of the polymer based on 1,2-epoxypropane and/or 1,2-epoxybutane in a solvent for the said polymer. By this technique of coating by the solvent route, it is possible to easily obtain composite electrodes with a thickness of less than 100 $\mu$m and, for example, of between 10 $\mu$m and 100 $\mu$m.

The polymer matrix of the composite electrode can optionally be crosslinked during the deposition of the composite electrode layer on the support by coating from the fluid phase. As indicated above, this crosslinking can be carried out by including a crosslinking agent, for example chemical generator of free radicals, triisocyanate or polyvalent element compound as mentioned above, in the fluid phase used for the coating or by subjecting the layer of fluid phase deposited on the support to the action of ionizing radiation.

In an embodiment of the iontophoresis device according to the invention which makes it possible to carry out the transcutaneous administration of a given total amount of an active principle to a subject, the electrode of one of the electrode assemblies is arranged in order to form a specific composite electrode, called a limiting composite electrode, which limiting electrode is a composite electrode according to the invention which contains a limited amount of the electrochemically consumable material, the said limited amount being chosen so that the amount of electricity necessary for its electrochemical consumption corresponds to the amount of electricity necessary to administer the given total amount of active principle to the subject, so that the circulation of the current between the electrodes is in practice interrupted when the consumable material of the limiting composite electrode has been consumed.

In the iontophoresis device according to the invention, a single one of the electrode assemblies, preferably the assembly containing the active principle, can be equipped with a reversible composite electrode according to the invention, the other electrode assembly containing a non-composite reversible electrode or even a non-reversible electrode, for example an electrode made from carbon, graphite, platinum, titanium or stainless steel. It is, however, preferable for each of the electrode assemblies of the iontophoresis device to be equipped with a composite electrode according to the invention, one of the electrode assemblies being furnished with a composite electrode adapted in order to act initially as anode, that is to say initially only containing a material consumable by electrochemical oxidation, and the other of the electrode assemblies being provided with a composite electrode adapted in order to act initially as cathode, that is to say initially only containing a material consumable by electrochemical reduction. It is also possible to envisage the case where each of the electrode assemblies of the iontophoresis device is equipped with a composite electrode according to the invention initially containing a couple of electrochemically consumable materials, the first being consumable by oxidation and the second being consumable by reduction, which are converted, the first into the second by electrochemical oxidation and the second into the first by electrochemical reduction, such a couple being, for example, Ag/AgCl. In this case, the electrode of each of the electrode assemblies can act initially as anode or cathode, depending on whether its polarity is positive or negative.

The electric generator applies, between the electrodes of the iontophoresis device, an electric signal which can be either an intensiometric signal, that is to say a signal of set average intensity, for example constant (intensiostatic signal), or, preferably, a potentiometric signal, that is to say a signal of set average voltage, for example constant (potentiostatic signal). The electric signal of the intensiostatic type or of the potentiostatic type can be continuous or pulsed and permanent or intermittent, with or without temporary polarity inversion. The frequency of the electric signal can range from 0 to 500 kHz and more particularly from 0 to 100 kHz.

Advantageously, the average voltage of the electric signal applied between the two electrodes, namely the active electrode and the back electrode, of the iontophoresis device is chosen between 0.1 and 50 volts and more especially between 0.5 and 20 volts, so that the density of the average current generated between the said electrodes has a value of less than 5 mA/cm$^2$ and more particularly of less than or equal to 1 mA/cm$^2$.

The electric signal generator of the iontophoresis device can be of any known type allowing generation of electric signals of set average intensity or of set average voltage which are continuous or pulsed and permanent or intermittent, with or without temporary polarity inversion, and which have the characteristics defined hereinabove.

The electrolyte, which is present in the active reservoir element in contact with the active composite electrode, advantageously contains an aqueous solution or an aqueous gel, adhesive or otherwise, which holds the active principle to be administered in an at least partially ionized form or in a neutral form. Likewise, the indifferent electrolyte, which is optionally in contact with the back electrode, is provided, at least in part, in the form of an aqueous solution or of an aqueous gel which is adhesive or otherwise. These aqueous solutions or gels can constitute the whole of the electrolyte present in the active reservoir element or the whole of the indifferent electrolyte or alternatively can form only a part of the said electrolytes and may then be dispersed in a non-aqueous medium forming the remainder of the electrolyte and chosen in order not to interrupt the ionic conducting continuity between the electrode and the skin and in order to increase the quality of the adhesion between the electrode and the skin. These aqueous solutions or aqueous gels can be obtained as is well known in iontophoresis techniques. Examples of aqueous gels or of thick aqueous solutions are in particular respectively described in the citations U.S. Pat. No. 4,764,164 and U.S. Pat. No. 3,163,166.

The aqueous medium holding the active principle, as well as the aqueous medium constituting the indifferent electrolyte, when the said electrolyte is used, can hold, if need be, various additives and in particular agents capable of promoting the transcutaneous passage of the active principle, such as, for example, vasodilating agents and/or amphiphilic agents, among which may be mentioned, without implied limitation, compounds of the alcohol type or of the ester type.

The use of composite electrodes according to the invention in the iontophoresis devices makes it possible to control the pH of the aqueous medium holding the active principle, as well as the pH of the aqueous medium constituting the indifferent electrolyte, which makes it possible to prevent or at the very least greatly reduce the introduction of foreign ions into the skin from the aqueous medium holding the active principle, as it is no longer necessary to use buffer agents.

The iontophoresis device according to the invention can be produced starting with any iontophoresis device, which has been modified in order to replace at least the electrode associated with the active reservoir holding the active principle, and preferably the active electrode and the back electrode, by a composite electrode according to the invention. If appropriate, the composite electrode of the iontophoresis device according to the invention can be arranged, as indicated above, in order to constitute a limiting electrode.

In particular, the device according to the invention can be a portable self-contained device, to be fixed by a bracelet or optionally to be stuck onto the skin, containing electrodes, at least one of which is a composite electrode according to the invention, each having an area of less than 50 cm$^2$ and more particularly of between 1 cm$^2$ and 40 cm$^2$, and a miniaturized electric signal generator. Thus, a self-contained portable device according to the invention can have a structure similar to that of the self-contained portable iontophoresis devices described, for example, in the citations U.S. Pat. No. 4,325,367, U.S. Pat. No. 4,557,723, EP-A-0,060,452 and FR-A-2,509,182, with the proviso that at least the active electrode associated with the active reservoir element holding the active principle is a composite electrode containing a polymer binder according to the invention, each of the electrodes of the said self-contained portable device, one of which can be arranged in order to constitute a limiting electrode, having an area of less than 50 cm$^2$ and more particularly of between 1 and 40 cm$^2$.

Each of the composite electrodes of the iontophoresis device can be perforated in the direction of the thickness by a plurality of microchannels produced, for example, mechanically by perforation of the electrode on conclusion of its manufacture or alternatively produced by incorporating a water-soluble porogenic agent in the electrode during the manufacture of the latter, as indicated in the citation WO-A-9116944. The presence of these microchannels in the composite electrode makes possible the production in the non-hydrated state of the reservoir element associated with the electrode and the subsequent hydration of the said reservoir element by passing water through the said channels.

When the electrode assemblies of the iontophoresis device are attached to the skin by means of an adhesive, this can be carried out by furnishing the face, intended to come into contact with the skin, of the reservoir element of each electrode assembly or an area surrounding the said face with a layer of an adhesive carrying the ions.

The iontophoresis device according to the invention allows transcutaneous administration to a subject of various active principles and, in particular, therapeutic molecules such as, for example, insulin, metoprolol, hydrocodone, tetracyclines, salbutamol, valproic acid, propanolol, arginine-desmopressin, desmopressin or others. More generally, the active principles which can be administered transcutaneously to a subject by resorting to the iontophoresis device according to the invention include the various products or compounds mentioned in pages 15 and 16 of the citation WO-A-9116944.

The invention is illustrated by the following examples, given without implied limitation.

EXAMPLE 1

Four series of electrodes which can be used as cathodes in an iontophoresis device were prepared, namely one series of composite electrodes according to the invention containing a binder composed of a 1,2-epoxypropane homopolymer (electrodes of 1A type), two series of control composite electrodes, one containing a binder composed of a polyisobutene (electrodes of 1B type) and the other a binder composed of an EVA copolymer (electrodes of 1C type), and finally one series of non-composite electrodes composed of a film of chloridized silver (electrodes of 1D type).

The electrodes were prepared as described hereinbelow.
ELECTRODES OF 1A TYPE PREPARED BY THE SOLVENT ROUTE 3.34 g of silver chloride powder having a particle size of between 5 μm and 50 μm, 0.335 g of carbon black, namely acetylene black YS sold by Shell Chimie, and 8.83 g of a 15% by weight solution of a 1,2-epoxypropane homopolymer (poly[1,2-oxypropylene]) in ethanol, the said homopolymer having a number-average molecular mass of approximately 100,000, and a few steel balls having a diameter of 6 to 10 mm were introduced into the 50 ml stainless steel chamber of a ball mill.

After milling for one hour, a homogeneous paste was obtained which was spread over a polyester film having a thickness of 80 μm by using a calibrated doctor which makes it possible to spread a wet thickness of approximately 500 μm.

After drying in a ventilated oven, a dry deposit, both adherent and flexible, was obtained on the polyester film which is highly resistant to the deformations of the support film. The coating deposited on the support exhibited a grammage of 9.425 mg/m$^2$, i.e. 6.29 mg of silver chloride per cm$^2$ capable of reduction to silver by passage of 1.18 mAh/cm$^2$. The film coated with the deposit based on the composition containing 1,2-epoxypropane homopolymer, silver chloride and carbon black was used for the manufacture of the electrodes of type A.

In order to do this, rectangles with a length of 5 cm and a width of 3 cm were cut out from the said coated film, that is to say coated with the above-mentioned deposit. A square of a self-adhesive insulating plastic film with a length per side of 3 cm and exhibiting, in its central part, a circular opening centred at the centre of the square and having a diameter of 16 mm, that is to say an area of 2 cm$^2$, was bonded to the coated face of each rectangle, the bonding of the square being carried out so that a side of the square coincided with a side edge of the rectangle. A conductive varnish based on silver was applied to the part of the coating situated outside the area delimited by the square, in order to facilitate the connection of the electrodes with the signal generator.

ELECTRODES OF TYPE 1B PREPARED BY THE SOLVENT ROUTE 3.442 g of silver chloride having the form of a powder with a particle size of between 5 μm and 50 μm, 0.343 g of graphite powder having a particle size of between 0.5 μm and 30 μm and 12.36 g of a 35% by weight solution of polyisobutene in hexane, the said polyisobutene having a number-average molecular mass of approximately 150,000, and a few steel balls with a diameter of 6 to 10 mm were introduced into the 50 ml stainless steel chamber of a ball mill.

After milling for one hour, a homogeneous paste was obtained which was spread over a polyester film having a thickness of 80 μm by using a calibrated doctor which makes it possible to spread a wet thickness of approximately 300 μm.

After drying in a ventilated oven, a dry deposit was obtained on the polyester film which exhibits good adhesion to the support film and which conforms, without becoming detached or tearing, to the deformations of the said support film. The coating deposited on the support film exhibited a grammage of 10.42 mg/cm$^2$, i.e. 6.95 mg of silver chloride per cm$^2$ capable of reduction to silver by passage of 1.2 mAh/cm$^2$.

Electrodes were prepared from the coated film obtained, as indicated in the present example for the electrodes of type 1A.

ELECTRODES OF TYPE 1C PREPARED BY THE SOLVENT ROUTE 3.44 g of silver chloride powder with a particle size of between 5 μm and 50 μm and 0.343 g of acetylene black YS were comilled for one hour in xylene by using a ball mill possessing a 50 ml stainless steel chamber. The mixture obtained was then added to a 10% by weight solution of an ethylene/vinyl acetate copolymer (EVA copolymer) in xylene maintained at 80° C., the said copolymer containing 8% by weight of vinyl acetate and having a number-average molecular mass of approximately 70,000, and the combination was homogenized at 80° C. using a propeller.

The paste obtained was spread at 80° C. over a polyester film having a thickness of 80 μm by using a calibrated doctor which makes it possible to spread a wet thickness of approximately 600 μm.

After drying in a ventilated oven, a coating was obtained on the polyester film which is homogeneous but which shows very little adhesion to the support, from which it becomes detached on bending. The said coating deposited on the support film exhibited a grammage of 9.93 mg/cm$^2$, i.e. 6.634 mg/cm$^2$ of silver chloride per cm$^2$ capable of reduction to silver by passage of 1.24 mAh/cm$^2$.

Electrodes were prepared from the coated film thus produced, as indicated above for the electrodes of type 1A.

ELECTRODES OF TYPE 1D

Non-composite electrodes having the same configuration as the composite electrodes of types 1A, 1B or 1C were prepared by replacing the coated polyester film used in the manufacture of the said composite electrodes by a film of electrochemically chloridized silver, one of the faces of which was masked by an insulating adhesive plastic film.

The electrochemically deposited silver chloride film exhibited a thickness of 15 μm and contained an amount of silver chloride corresponding to an amount of electricity equal to 1.25 mAh/cm$^2$.

In order to carry out the electrochemical chloridation of the silver film, a direct electric current was passed between the said silver film and a graphite rod both immersed in a bath of 1N hydrochloric acid, the first being connected to the positive pole and the second to the negative pole of a generator of the direct electric current, the electric current being passed for 15 minutes with a current density equal to 5 mA/cm$^2$.

The various electrodes obtained as indicated above were subjected to capacity evaluation tests.

In order to evaluate the true capacity of the electrodes, each electrode to be studied was introduced into a cell in the form of a parallelepipedal vessel containing a 1% by weight aqueous NaCl solution, so as to be immersed to a depth of 2.5 cm in the said solution and thus to exhibit an electrochemically active area equal to 2 cm$^2$. A complementary electrode with a structure and area similar to the electrode to be studied but constructed, as indicated for the electrode 1D, from a sheet of silver chloridized by electrochemical oxidation in order to contain an amount of silver chloride equivalent to 2 mAh/cm$^2$ was also immersed in the aqueous solution to the same depth as the electrode to be studied. The said electrode to be studied and the complementary electrode were each connected to one of the poles of a direct electric current generator delivering an electric current of constant intensity. A milliammeter and a voltameter were mounted in series with the electric current generator and a millivoltmeter was arranged in order to measure the difference in potential at the terminals of the electrode to be studied and of the complementary electrode.

Studies of cutaneous tolerance of iontophoretic electric signals have shown that it can be very useful to reverse the direction of the current a number of times during the iontophoretic treatment. Consequently, the capacity of each type of electrode to be studied was evaluated successively in the direct direction and then in the reverse direction, with a current density of 0.25 mA/cm$^2$.

The successive capacities observed in each cycle for the direct direction (operating as cathode) and for the reverse direction (operating as anode), before the electrode to be studied becomes irreversible, that is to say at the moment where it begins to cause an over-potential (in the region of 300 mV), accompanied by electrolysis of the water causing an increase in the pH in the vessel, as well as the duration of each cycle of operating as cathode (cathode cycle) or as anode (anode cycle), the total duration of the exchange and the total capacity exchanged are given in Table I hereinbelow.

TABLE I

| Nature of the electrode | Type 1A | Type 1B | Type 1C | Type 1D |
|---|---|---|---|---|
| Binder | POP[a)] | PIB[b)] | EVA[c)] | None[d)] |
| Theoretical capacity as cathode (mAh/cm$^2$) | 1.18 | 1.3 | 1.24 | 1.25 |
| Theoretical duration at 0.25 mA/cm$^2$ (hours) | 4.72 | 5.20 | 4.95 | 5 |
| Duration, 1st cathode cycle (hours) | 4.67 | 3.67 | 0.3 | 3.75 |
| Use of the theoretical capacity | 98% | 70.5% | 6% | 75% |
| Duration, 1st anode cycle (hours) | 3.34 | 0.75 | 0.06 | 2.67 |
| Duration, 2nd cathode cycle (hours) | 3.25 | 0.42 | 0.05 | 2 |
| Use of the theoretical capacity | 70% | 11% | 1% | 40% |
| Duration, 2nd anode cycle (hours) | 2.25 | 0.25 | 0 | 1.42 |
| Duration, 3rd cathode cycle (hours) | 2.17 | 0.05 | 0 | 1 |
| Use of the theoretical capacity | 46% | 1% | | 20% |
| Duration, 3rd anode cycle (hours) | 1.5 | 0 | | 0.75 |
| Duration, 4th cathode cycle (hours) | 1.42 | 0 | | 0.5 |
| Use of the theoretical capacity | 30% | | | 10% |
| Duration, 4th anode cycle (hours) | 1 | | | 0.41 |
| Total duration of the exchange (hours) | 19.60 | 5.14 | 0.41 | 12.50 |
| Total capacity exchange (mAh) | 4.9 | 1.3 | 0.1 | 3.12 |

[a)]POP = 1,2-epoxypropane homopolymer
[b)]PIB = polyisobutene
[c)]EVA = ethylene/vinyl acetate copolymer
[d)]non-composite electrode made of chloridized silver (Ag/AgCl)

Comparison of the results collated in Table I emphasizes the major advantage of a binder according to the invention, in the present case 1,2-epoxypropane homopolymer, for the preparation of composite electrodes. Indeed, the levels of use of the theoretical capacity, itself related to the amounts of silver chloride deposited per unit of area, are markedly higher than for composite electrodes containing polyisobutene or EVA copolymer binder or than for non-composite electrodes made of chloridized silver. It is the same for the capacity which can be used in the reverse direction, that is to say the ability to continue to operate reversibly during current inversion, because, in this case again, the binder according to the invention results in composite electrodes which are markedly better behaved than the other binders, such as polyisobutene or EVA copolymer. It was observed that the latter polymer is particularly poorly suited to the preparation of composite electrodes by the solvent route, probably due to its crystallinity, which results in its precipitation during spreading of the paste before the latter has had the time to fully bond the silver chloride particles.

It should also be emphasized that, while the material cost of the various composite electrodes are substantially the same, it is not the same for the non-composite electrodes made of chloridized silver (electrodes of type 1D), which require, in order to retain acceptable mechanical strength, that less than half the silver is chloridized and consequently that the silver films used have a thickness of at least 10 $\mu$m to 15 $\mu$m, which represents an amount of silver of 10 to 25 mg/cm$^2$ which is not involved in the electrochemical process, but triples the cost of these electrodes with respect to the composite electrodes, and which is entirely lost because the iontophoresis electrodes are used only once.

EXAMPLE 2

Two series of mixed composite electrodes, that is to say which can be used without distinction as anodes or as cathodes, namely one series of composite electrodes according to the invention containing a binder composed of a copolymer of 1,2-epoxypropane and of allyl glycidyl ether (electrodes of type 2A) and one series of control composite electrodes containing a binder composed of polyisobutene (electrodes of type 2B), were prepared by the solvent route.

The electrodes were manufactured as follows:

Electrodes of Type 2A 25.4 g of a 15% by weight solution of a copolymer of 1,2-epoxypropane and of allyl glycidyl ether in ethanol, the said copolymer containing 2 molar % of allyl glycidyl ether and exhibiting a number-average molecular mass of approximately 100,000, as well as 0.965 g of acetylene black YS, 5.35 g of silver chloride powder with a particle size of between 5 $\mu$m and 50 $\mu$m and 8.06 g of silver powder with a particle size of between 5 $\mu$m and 50 $\mu$m were introduced into the 50 ml stainless steel chamber of a ball mill. A few stainless steel balls with a diameter of 6 to 10 mm were also introduced into the chamber and the said chamber was then placed under agitation for approximately a half-hour.

The suspension obtained was spread over a polyester film with a thickness of 80 $\mu$m using a doctor adjusted to 300 $\mu$m. The coating produced had the appearance of a paint resulting after drying, carried out in a ventilated oven, in a black, flexible and homogeneous film of a composite deposit which adheres well to the polyester support film and which has a thickness of approximately 50 $\mu$m. This composite deposit had a grammage of 12.32 mg/cm$^2$, including an amount of silver, which can be used as anode, equivalent to 1.3 mAh/cm$^2$ and an amount of silver chloride, which can be used as cathode, equivalent to 0.65 mAh/cm$^2$.

Electrodes were manufactured, from the polyester film coated with the composite deposit, which have the configuration and the dimensions of the electrodes of the type 1A of Example 1, the electrodes being assembled as indicated in the said Example 1.

Electrodes of Type 2B

The preparation was carried out as indicated for the production of electrodes of type 2A, the solution of copolymer of 1,2-epoxypropane and of allyl glycidyl ether being replaced, however, by 11 g of a 35% by weight solution in hexane of the polyisobutene used in Example 1 and the doctor used for spreading over the polyester film being adjusted to 250 $\mu$m.

The coating produced resulted, after drying, in a black, homogeneous and flexible film of a composite deposit which adheres to the polyester support film and which has a thickness of 45 $\mu$m. This composite deposit had a grammage of 14.2 mg/cm$^2$, including an amount of silver, which can be used as anode, equivalent to 1.56 mAh/cm$^2$ and an amount of silver chloride, which can be used as cathode, equivalent to 0.78 mAh/cm$^2$.

Comparative cycling of the two types of electrodes

Two electrodes of type 2A or two electrodes of type 2B, each electrode exhibiting an electrochemically active area of 2 cm$^2$, were immersed in a cell analogous to that used for the evaluation of the electrodes of Example 1 and thus filled with a 1% by weight aqueous NaCl solution, and the two electrodes of the cell were connected to a system imposing a direct current of 0.5 mA between the said electrodes with reversion of the direction of the current every 30 minutes, which corresponds to the passage, in each direction, of an amount of current of 0.125 mAh/cm² for each electrode. A probe immersed at the centre of the cell made it possible to measure and to record the pH of the medium and a millivoltmeter mounted at the terminals of the electrodes made it possible to monitor the difference in potential appearing at the terminals of the cell.

With a cell equipped with electrodes of type A, neither an abnormal variation in the pH nor a rise in the difference in potential at the cycle end was recorded during 8 hours, i.e. 8 complete cycles and 14 reversions in the direction of the current.

With a cell equipped with electrodes of type B, although these electrodes have a theoretical capacity slightly greater than that of the electrodes of type A, rises in the difference in potential at the terminals of the cell were observed before even the third change of polarity and a rapid decrease in the pH from the middle of the fourth cycle, i.e. before the end of the second hour of operation.

EXAMPLE 3

Two series of composite electrodes which can be used as cathodes in an iontophoresis device were prepared by the molten route, namely a series of composite electrodes according to the invention containing a binder composed of a 1,2-epoxypropane homopolymer (electrode of type 3A) and a series of control composite electrode containing a binder composed of an EVA copolymer (electrodes of type 3C).

The electrodes were manufactured as follows:
Electrodes of Type 3A 23.5 g of a 1,2-epoxypropane homopolymer having a number-average molecular mass of approximately 180,000, then 20.3 g of unsized carbon fibres having a diameter of 8 μm and an average length of 6 mm and, finally, 62.6 g of silver chloride powder with a particle size of between 5 μm and 50 μm were introduced into the 50 ml chamber of a Brabender mixer (Brabender Instruments Inc., South Hachensack, N.J., United States) maintained at 120° C. The mixture thus produced was homogenized in the mixer for 20 minutes, before being extracted from the said mixer and cut up into particles which were then moulded between two poly(ethylene terephthalate) films, the moulding being carried out in a hydraulic press, the temperature of which was adjusted to 120° C. and the pressure to 2 tonnes.

After 5 pressure cycles at 2 tonnes, interrupted by periods of relaxation, a composite product film was obtained, the thickness of which was in the region of 80 μm, the grammage of which was equal to 19.11 mg/cm² and the amount of silver chloride, which can be used as cathode, of which was equivalent to 2.1 mAh/cm².

From the composite product film, one of the faces of which was masked by an insulating adhesive plastic film, electrodes were produced having the configuration and the dimensions of the electrodes of the type 1A, the electrodes being assembled as indicated in Example 1.
Electrodes of type 3C The preparation was carried out as indicated for the production of the electrodes of type 3A, the 1,2-epoxypropane homopolymer being replaced, however, by the same amount of the copolymer of ethylene and of vinyl acetate (EVA copolymer) used in Example 1, the chamber of the mixer being adjusted to 135° C. and the temperature of the moulding press being adjusted to 165° C.

After 5 pressure cycles, interrupted by periods of relaxation, a composite product film was obtained, the thickness of which was in the region of 95 μm and the grammage of which was equal to 22.8 mg/cm², the amount of silver chloride, which can be used as cathode, being equivalent to 2.5 mAh/cm².

From the said composite film, masked on one face by an insulating adhesive plastic film, electrodes were produced having the configuration and the dimensions of the electrodes of type 1A, the procedure being as indicated in Example 1.
Comparison of the levels of use of the electrodes as cathodes and then on cycling By using the procedure described in Example 1, the capacity of the composite electrodes of type 3A and of type 3C, used as cathode, was evaluated by measuring the maximum amount of current which can be passed per unit of area of electrode before the appearance of the phenomena related to electrolysis of the water, namely rise in the difference in potential at the terminals of the cell and appearance of a substantial variation in the pH in the cell. The capacity of each type of electrode 3A and 3C was studied at a constant current density equal to 0.3 mA/cm², the electrochemically active area of each electrode representing 2 cm².

The capacities observed after each cycle of operation as cathode, as well as the maximum duration observed for each cycle of operation as cathode or as anode, the total duration of the exchange, the total capacity exchanged and the percentage of the total capacity exchanged, are given in Table II hereinbelow.

TABLE II

| Nature of the electrode | Type 3A | Type 3C |
|---|---|---|
| Binder | POP | EVA |
| Theoretical capacity as cathode (mAh/cm²) | 2.1 | 2.5 |
| Theoretical duration at 0.3 mA/cm² (hours) | 7 | 8.33 |
| Duration, 1st cathode cycle (hours) | 6.92 | 8.18 |
| Use of the theoretical capacity | 99% | 98% |
| Duration, 1st anode cycle (hours) | 1.73 | 0.60 |
| Duration, 2nd cathode cycle (hours) | 1.63 | 0.23 |
| Use of the theoretical capacity | 23% | 2.8% |
| Duration, 2nd anode cycle (hours) | 0.47 | 0.04(*) |
| Duration, 3rd cathode cycle (hours) | 0.40 | |
| Use of the theoretical capacity | 5.7% | |
| Duration, 3rd anode cycle (hours) | 0.13 | |
| Duration, 4th cathode cycle (hours) | 0.10 | |
| Total duration of exchange (hours) | 11.38 | 9.05 |
| Total capacity exchanged (mAh) | 3.41 | 2.7 |
| % of the total capacity exchanged | 162% | 108% |

(*) appearance of a very rapid decrease in the pH in the cell

Examination of the results in Table II shows that, while the performances of the electrodes of type 3A and of type 3C are similar during the first use, the cyclability of the electrodes 3A using a binder according to the invention (1,2-epoxypropane homopolymer) is very markedly superior to that of the electrodes of type 3C using a binder according to the state of the art (EVA copolymer), which implies that the binder according to the invention has a much better performance than the binder according to the state of the art.

Moreover, if the results of the present example are compared with those of Example 1, it is also found that the composite electrodes according to the invention obtained by the solvent route (electrode 1A) are superior, especially as regards cyclability, to the composite electrodes according to the invention obtained by the molten route.

For the same capacity of an electrode which can be used both in a single direction and during treatments with frequent reversions of the direction of the current, the polymer binders according to the invention for composite electrodes which can be used in iontophoresis are very much superior to the polymer binders, in particular polyisobutene or EVA copolymers, of the state of the art. This superiority is still more evident when the said electrodes are obtained by the solvent route, a technique which makes it possible to obtain composite electrodes of low thicknesses corresponding to theoretical capacities of less than 1.5 mAh/cm$^2$.

EXAMPLE 4

The transcutaneous diffusion of sodium valproate was studied by iontophoresis using electrodes, one of which was a composite electrode of type 1A or of type 1C.

The operations were carried out in iontophoresis cells of identical structure. Each iontophoresis cell consisted of three coaxial adjacent cylindrical compartments of 2 cm$^2$ cross-section, namely, in this order, a donor compartment, a receiver compartment and a back-electrode compartment, these three compartments being separated, each from the following and in a leaktight manner, by a piece of nude rat (OFA hr/hr) skin which is used as the membrane for the transcutaneous diffusion study. The donor compartment, with a volume of 0.5 ml, contained a 10% by weight aqueous sodium valproate solution. The receiver compartment, with a volume of 10 ml, contained physiological salt solution to which 500 ppm by weight of NaN$_3$ had been added and was stirred using a magnetic bar. The back-electrode compartment, identical to the donor compartment, contains 0.5 ml of an aqueous solution containing 2% by weight of NaCl and 500 ppm by weight of NaN$_3$. At its end opposite the receiver compartment, the donor compartment was equipped, depending on the situation, with a composite electrode of type 1A or of type 1C according to Example 1 and exhibiting an active area equal to 2 cm$^2$. The back-electrode compartment was equipped with a non-composite electrode of type 1D according to Example 1 and exhibiting an active area equal to 2 cm$^2$. The active face of each electrode was turned towards the rat-skin membrane side.

The samples of rat skin had had all the subcutaneous tissue removed and had been preserved by freezing at −40° C. until they were mounted in the iontophoresis cell, with the dermal faces turned towards the receiver compartment, after having spent 15 minutes at room temperature in physiological salt solution with 0.05% by weight of NaN$_3$ added.

For each of the tests carried out, four identical iontophoresis cells were started up simultaneously. The effective exchange area was 2 cm$^2$ for each skin.

A direct current generator, the negative pole of which was connected to the composite electrode, made it possible to establish an electric signal of set intensity equal to 0.2 mA between the electrodes of each cell.

The iontophoresis operation was continued until the appearance of a difference in potential equal to 0.8 volt at the terminals of the iontophoresis cell and the passage of the current was then halted by opening the circuit.

After time periods, calculated from the beginning of the iontophoresis operation, equal to 1 hour, 12 hours and 24 hours respectively, 0.5 ml of the liquid contained in the receiver compartment of the iontophoresis cell was removed and the amount of sodium valproate contained in each of the samples was quantitatively determined. From the values obtained by quantitative determination, the total amount of valproate which had passed into the receiver compartment of the iontophoresis cell at the end of the said time periods was calculated.

The results obtained, averaged over four tests, are given in Table III.

TABLE III

| Nature of the cathode | 1A | 1C |
|---|---|---|
| Theoretical capacity (mAh/cm$^2$) | 1.18 | 1.24 |
| Theoretical duration at 0.1 mA/cm$^2$ (hours) | 11.8 | 12.4 |
| True average duration (hours) | 11.4 | 0.75 |
| Amount of valproate which has passed into the receiver compartment (mg): | | |
| at 1 hour | 0.2 | 0.16 |
| at 12 hours | 2.4 | 0.25 |
| at 24 hours | 2.9 | 0.28 |

Examination of the results which appear in Table III clearly emphasizes the superiority of the composite electrodes according to the invention, which can operate for markedly longer than the composite electrodes of comparable capacities obtained according to the state of the art before the appearance of the undesirable phenomena related to electrolysis of water.

We claim:

1. Iontophoresis device for the transcutaneous administration of an active principle to a subject comprising a first electrode assembly composed of a first electrode, called the active electrode, in contact with an active reservoir element adapted to contain an electrolyte holding the active principle in an at least partially ionized form or in a neutral form and to ensure, when it is placed in contact with an area of the skin of the subject, ionic conducting continuity between the said first electrode and the said area, a second electrode assembly composed of a second electrode, called the back electrode, or of such a second electrode in contact with a reservoir element arranged to hold, at least an electrolyte and to ensure, when it is placed in contact with a portion of the skin of the subject, ionic conducting continuity between the second electrode and the said portion, and an electric signal generator which can be connected to each of the said first and second electrodes, so that the first electrode has the same polarity as the ions of the active principle or a positive polarity if the said active principle is neutral and so that the second electrode has a polarity opposite to that of the first electrode, the first electrode in contact with the active reservoir element and/or the second electrode in contact with the reservoir element associated with it being composed of a composite electrode comprising a polymer binder and, as percentages by volume of the said binder, from 4% to 60% of an electrochemically non-consumable pulverulent or fibrous conductive filler and from 4% to 100% of a divided material consumable by electrochemical oxidation or reduction, wherein the polymer binder of the composite electrode or of each of the composite electrodes comprises at least one polymer based on 1,2-epoxypropane and/or 1,2-epoxybutane and containing, in molar percentages, from 60% to 100% of 1,2-epoxypropane and/or 1,2-epoxybutane and from 40% to 0% of one or a number of other monomers copolymerizable with 1,2-epoxypropane and 1,2-epoxybutane.

2. Device according to claim 1, wherein the polymer or polymers constituting the polymer binder of the composite electrode have a molar content of 1,2-epoxypropane and/or 1,2-epoxybutane ranging from 75% to 100%.

3. Device according to claim 1 wherein the polymer or polymers constituting the polymer binder of the composite electrode are chosen from homopolymers of 1,2-epoxypropane or of 1,2-epoxybutane or alternatively statistical copolymers, sequential copolymers or sequential copolymers containing statistical junctions of 1,2-epoxypropane and of 1,2-epoxybutane with one another and/or with one or a number of cyclic monomers chosen from the group formed from (i) cyclic oxides, the ring of which contains more than three members, and (ii) cyclic oxides of formula

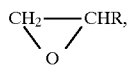

in which R is an $R_1$ radical or a $CH_2$—O—$R_2$—$R_1$ radical, with $R_1$ denoting a hydrogen atom or a $C_3$ to $C_{12}$, and $R_2$ representing a polyether radical of formula —($CH_2$—$CH_2$—O$)_p$— where p denotes a number ranging from 0 to 10 and preferably from 0 to 4.

4. Device according to claim 3, wherein the cyclic monomers, copolymerized with 1,2-epoxypropane and/or 1,2-epoxybutane, are chosen from oxetane, tetrahydrofuran, dioxolane, dioxane and the cyclic oxides of formula

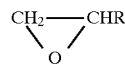

in which R is a propyl, butyl, —$CH_2OCH_3$ or —$CH_2OCH_2$—$CH$=$CH_2$ radical.

5. Device according to claim 1, wherein the polymer or polymers constituting the polymer binder of the composite electrode are homopolymers of 1,2-epoxypropane or of 1,2-epoxybutane or copolymers of the said oxides with one another.

6. Device according to claim 1, wherein the polymer binder of the composite electrode is crosslinked.

7. Device according to claim 1, wherein the polymer or polymers constituting the polymer binder of the composite electrode have molecular masses, in the non-crosslinked state, of between 10,000 and $10^6$.

8. Device according to claim 1, wherein the electrochemically nonconsumable pulverulent or fibrous conductive filler is composed of a conductive material formed from at least one product selected from carbon black, graphite or boron.

9. Device according to claim 1, wherein the conductive filler of the composite electrode is a pulverulent filler which is provided in the form of a powder with a particle size of less than 100 µm.

10. Device according to claim 1, wherein the conductive filler of the composite electrode is a fibrous filler which is provided in the form of short fibres having a diameter ranging from 1 pm to 15 µm and a ratio of the length to the diameter, expressed in the same unit of length, ranging from 50 to 1000.

11. Device according to claim 1, wherein the electrochemically consumable material present in the composite electrode is consumable by electrochemical oxidation, the said composite electrode constituting an anode.

12. Device according to claim 11, wherein the material consumable by electrochemical oxidation present in the composite electrode is a metal chosen from Ag, Zn, Cu, Ni, Sn, Pb, Fe and Cr.

13. Device according to claim 1, wherein the electrochemically consumable material present in the composite electrode is consumable by electrochemical reduction, the said composite electrode constituting a cathode.

14. Device according to claim 13, wherein the material consumable by electrochemical reduction present in the composite electrode consists of AgCl or CuCl.

15. Device according to claim 1, wherein the electrochemically consumable material present in the composite electrode comprises the couple composed of an ionizable compound of a metal, giving metal ions which are electrochemically reducible to the metal, and of the said metal, the said electrode constituting without distinction an anode or a cathode, which couple is the Ag/AgCl couple.

16. Device according to claim 1, wherein the electrochemically consumable material present in the composite electrode is a powder, the particle size of which is less than 100 µm.

17. Device according to claim 1, wherein the proportions of electrochemically non-consumable conductive filler and of electrochemically consumable material associated with the polymer binder in order to constitute the composite electrode represent, by volume of the polymer binder, 8% to 45% for the conductive filler and 25% to 70% for the electrochemically consumable material.

18. Device according to claim 1, wherein the composite electrode or the composite electrodes which it contains have a thickness of less than 100 µm.

19. Device according to claim 1, wherein the composite electrode or the composite electrodes which it contains are produced by a coating technique by the solvent route.

20. Device according to claim 1, wherein the generator of electric signals applies, between the electrodes, an intensiometric signal, that is to say a signal of set average intensity, or a potentiometric signal, that is to say a signal of set average voltage, the said signal being continuous or pulsed and permanent or intermittent, with or without temporary polarity inversion, and having a frequency ranging from 0 to 500 kHz.

21. Device according to claim 20, wherein the electric signal applied between the electrodes has an average voltage of between 0.1 and 50 volts and more especially between 0.5 and 20 volts, so that the density of the average current generated between the said electrodes has a value of less than 5 mA/cm$^2$.

22. Electrode assembly for iontophoresis comprising a composite electrode in contact with a reservoir element adapted, on the one hand, in order to contain an electrolyte, the said electrolyte holding an active principle in an at least partially ionized form or in a neutral form or being an indifferent electrolyte, and, on the other hand, in order to ensure, when it is placed in contact with an area of the skin of a subject, ionic conducting continuity between the said composite electrode and the said area, which composite electrode is formed from a composition composed of a polymer binder and, by volume of the said binder, from 4% to 60% of an electrochemically non-consumable pulverulent or fibrous conductive filler and from 4% to 100% of a divided material consumable by electrochemical oxidation or reduction, the said assembly being characterized in that the polymer binder of the composite electrode comprises at least one polymer based on 1,2-epoxypropane and/or 1,2-epoxybutane and containing, in molar percentages, from 60% to 100% of 1,2-epoxypropane and/or 1,2-epoxybutane and from 40% to 0% of one or a number of other monomers copolymerizable with 1,2-epoxypropane and/or 1,2-epoxybutane.

23. Electrode assembly according to claim 22, wherein the polymer or polymers constituting the polymer binder of the composite electrode have a molar content of 1,2-epoxypropane and/or 1,2-epoxybutane ranging from 75% to 100%.

24. Electrode assembly according to claim 22 wherein the polymer or polymers constituting the polymer binder of the composite electrode are chosen from homopolymers of 1,2-epoxypropane or of 1,2-epoxybutane or alternatively statistical copolymers, sequential copolymers or sequential copolymers containing statistical junctions of 1,2-epoxypropane and of 1,2-epoxybutane with one another and/or with one or a number of cyclic monomers chosen from the group formed from (i) cyclic oxides, the ring of which contains more than three members, and (ii) cyclic oxides of formula

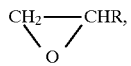

in which R is an $R_1$ radical or a $CH_2$—O—$R_2$—$R_1$ radical, with $R_1$ denoting a hydrogen atom or a $C_3$ to $C_{12}$, and $R_2$ representing a polyether radical of formula —$(CH_2$—$CH_2$—$O)_p$— where p denotes a number ranging from 0 to 10.

25. Electrode assembly according to claim 24, wherein the cyclic monomers, copolymerized with 1,2-epoxypropane and/or 1,2-epoxybutane, are chosen from oxetane, tetrahydrofuran, dioxolane, dioxane and the cyclic oxides of formula

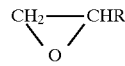

in which R is a propyl, butyl, —$CH_2OCH_3$ or —$CH_2OCH_2$—$CH$=$CH_2$ radical.

26. Electrode assembly according to claim 22, wherein the polymer or polymers constituting the polymer binder of the composite electrode are homopolymers of 1,2-epoxypropane or of 1,2-epoxybutane or copolymers of the said oxides with one another.

27. Electrode assembly according to claim 22, wherein the polymer binder of the composite electrode is crosslinked.

28. Electrode assembly according to claim 22, wherein the polymer or polymers constituting the polymer binder of the composite electrode have molecular masses, in the non-crosslinked state, of between 10,000 and $10^6$.

29. Electrode assembly according to claim 22, wherein the electrochemically nonconsumable pulverulent or fibrous conductive filler is composed of a conductive material formed from at least one product selected from carbon black, graphite or boron.

30. Electrode assembly according to claim 22, wherein the conductive filler of the composite electrode is a pulverulent filler which is provided in the form of a powder with a particle size of less than 100 μm.

31. Electrode assembly according to claim 22, wherein the conductive filler of the composite electrode is a fibrous filler which is provided in the form of short fibres having a diameter ranging from 1 μm to 15 μm and a ratio of the length to the diameter, expressed in the same unit of length, ranging from 50 to 1000.

32. Electrode assembly according to claim 22, wherein the electrochemically consumable material present in the composite electrode is consumable by electrochemical oxidation, the said composite electrode constituting an anode, the said material consumable by electrochemical oxidation being more particularly a metal chosen from Ag, Zn, Cu, Ni, Sn, Pb, Fe and Cr.

33. Electrode assembly according to claim 22, wherein the electrochemically consumable material present in the composite electrode is consumable by electrochemical reduction, the said composite electrode constituting a cathode, the said material consumable by electrochemical reduction consisting of AgCl or CuCl.

34. Electrode assembly according to claim 22, wherein the electrochemically consumable material present in the composite electrode comprises the couple composed of an ionizable compound of a metal, giving metal ions which are electrochemically reducible to the metal, and of the said metal, the said electrode constituting without distinction an anode or a cathode, which couple is the Ag/AgCl couple.

35. Electrode assembly according to claim 22, wherein the electrochemically consumable material present in the composite electrode is a powder, the particle size of which is less than 100 μm.

36. Electrode assembly according to claim 22, wherein the proportions of electrochemically non-consumable conductive filler and of electrochemically consumable material associated with the polymer binder in order to constitute the composite electrode represent, by volume of the polymer binder, 8% to 45% for the conductive filler and 25% to 70% for the electrochemically consumable material.

37. Electrode assembly according to claim 22, wherein the composite electrode which it contains has a thickness of less than 100 μm.

38. Electrode assembly according to claim 22, wherein the composite electrode which it contains is produced by a coating technique by the solvent route.

* * * * *

UNITED STATES PATENT AND TRADEMARK OFFICE
CERTIFICATE OF CORRECTION

PATENT NO. : 5,807,305
DATED : September 15, 1998
INVENTOR(S) : Daniel MULLER et al.

It is certified that error appears in the above-indentified patent and that said Letters Patent is hereby corrected as shown below:

In the Abstract (item [57]), line 6, change "10-100 mo %" to --60-100 mol%--.

Column 19, line 21, after "$C_{12}$", insert --alkyl or $C_2$ to $C_{12}$ alkenyl radical--.

Column 21, line 20, after "$C_{12}$", insert --alkyl or $C_2$ to $C_{12}$ alkenyl radical--.

Signed and Sealed this

Twentieth Day of April, 1999

Attest:

Q. TODD DICKINSON

*Attesting Officer*   *Acting Commissioner of Patents and Trademarks*